US008492137B2

(12) United States Patent
Link et al.

(10) Patent No.: US 8,492,137 B2
(45) Date of Patent: Jul. 23, 2013

(54) COVER FOR SAMPLE WITH HOMOGENOUS PRESSURE APPLICATION

(75) Inventors: Holger Link, Hamburg (DE); Jens Peter Kroog, Grosshansdorf (DE); Lutz Timmann, Fuhlendorf (DE); Henner Tasch, Hamburg (DE); Cordula Kroll, Tangstedt (DE); Stefan Roth, Stuttgart (DE); Ruediger Huhn, Luebeck (DE); Reinhold Goetz, Hamburg (DE); Helmut Knofe, Norderstedt (DE); Arne Schafrinski, Bad Oldesloe (DE)

(73) Assignee: Eppendorf AG, Hamburg (DE)

( * ) Notice: Subject to any disclaimer, the term of this patent is extended or adjusted under 35 U.S.C. 154(b) by 1484 days.

(21) Appl. No.: 12/030,105

(22) Filed: Feb. 12, 2008

(65) Prior Publication Data

US 2009/0155855 A1 Jun. 18, 2009

Related U.S. Application Data

(60) Provisional application No. 60/889,624, filed on Feb. 13, 2007.

(30) Foreign Application Priority Data

Feb. 13, 2007 (EP) .................................... 07003050

(51) Int. Cl.
*C12M 1/34* (2006.01)
*C12M 3/00* (2006.01)

(52) U.S. Cl.
USPC .................. 435/287.2; 435/287.1; 435/287.3; 435/288.3; 435/288.7

(58) Field of Classification Search
USPC ....... 435/287.1–287.3, 288.3–288.7; 100/211
See application file for complete search history.

(56) References Cited

U.S. PATENT DOCUMENTS 4,096,965 A 6/1978 Lessnig et al.
5,056,427 A * 10/1991 Sakabe et al. ................. 100/211

(Continued)

FOREIGN PATENT DOCUMENTS

CA 2610732 12/2006
DE 20117661 U1 4/2003

(Continued)

OTHER PUBLICATIONS

Chapter 9 ("Gehemme und Gesperre") of "Konstrucktionselemente der Feinmechanik" 9Ed.: Werner Krause; ISBN: 3-341-00461-0), pp. 445-460 (English Translation).

(Continued)

*Primary Examiner* — Michael Marcheschi
*Assistant Examiner* — Shanta G Doe
(74) *Attorney, Agent, or Firm* — Arnold & Porter LLP; Todd Lorenz

(57) ABSTRACT

The present invention relates to a cover for covering one or more sample(s) that are suitable to avoid or minimize evaporation and/or condensation of any vaporizable substance that may be present in the sample(s) or reaction mixture(s), in particular evaporation of substance at the fringes of a vessel or an array of vessels or condensation of a substance on the lid of a reaction vessel or a plate/block containing the sample(s) and/or a cover. This is achieved by providing a device comprising, among others, a force distribution unit that comprises at least one medium or material that is unable to withstand a static shear stress and deforms continuously under the action of a shear force.

18 Claims, 9 Drawing Sheets

U.S. PATENT DOCUMENTS

| | | | | |
|---|---|---|---|---|
| 5,475,610 | A | | 12/1995 | Atwood et al. |
| 5,575,610 | A | | 11/1996 | Soyama |
| 5,851,492 | A | * | 12/1998 | Blattner ........................ 422/569 |
| 6,153,426 | A | | 11/2000 | Heimberg |
| 6,197,572 | B1 | | 3/2001 | Schneebeli |
| 6,518,060 | B2 | | 2/2003 | Heimberg et al. |
| 6,677,151 | B2 | | 1/2004 | Sandell |
| 6,703,236 | B2 | | 3/2004 | Atwood |
| 6,730,883 | B2 | | 5/2004 | Brown et al. |
| 2005/0226782 | A1 | | 10/2005 | Reed et al. |

FOREIGN PATENT DOCUMENTS

| | | | |
|---|---|---|---|
| EP | 0388159 | A2 | 9/1990 |
| EP | 0955097 | A1 | 11/1999 |
| EP | 1013342 | A2 | 6/2000 |
| EP | 1045038 | A | 10/2000 |
| WO | WO 03059517 | A2 | 7/2003 |
| WO | WO 2006002226 | A1 | 1/2006 |
| WO | WO 2006133750 | | 12/2006 |

OTHER PUBLICATIONS

Examination Report, Australian Patent Office, regarding Singapore Patent Application No. SG 200801182, held in the name of Eppendorf AG (DE), mailed Jan. 15, 2010.

Search Report and Written Opinion, Australian Patent Office, regarding Singapore Patent Application No. SG 200801182, held in the name of Eppendorf AG (DE), mailed Apr. 7, 2009.

Extended European Search Report, European Patent Office, regarding European Patent Application No. 07003050, held in the name of Eppendorf AG (DE), mailed Jul. 6, 2007.

Examination Report, European Patent Office, regarding European Patent Application No. 07003050, held in the name of Eppendorf AG (DE), mailed Sep. 20, 2010.

Extended European Search Report, European Patent Office, regarding European Patent Application No. 07003049, held in the name of Eppendorf AG (DE), mailed Jul. 4, 2007.

Examination Report, European Patent Office, regarding European Patent Application No. 07003049, mailed Sep. 20, 2010.

Examination Report, Australian Patent Office, regarding Singapore Patent Application No. SG 200801180, held in the name of Eppendorf AG (DE), mailed Sep. 8, 2010.

Written Opinion and International Search Report, Australian Patent Office, regarding Singapore Patent Applicaton No. 200801180, held in the name of Eppendorf AG (DE), mailed Feb. 19, 2009.

Written Opinion, Australian Patent Office, regarding Singapore Application No. 200801180, held in the name of Eppendorf AG (DE), mailed Nov. 25, 2009.

* cited by examiner

COVER FOR SAMPLE WITH HOMOGENOUS PRESSURE APPLICATION

CROSS-REFERENCE TO RELATED APPLICATIONS

This application claims the benefit under 35 U.S.C. §119 (e) of U.S. Provisional Application Ser. No. 60/889,624 filed Feb. 13, 2007 and 35 U.S.C. §119(b) of European Patent Application 07003050.7 filed Feb. 13, 2007.

FIELD OF THE INVENTION

The present invention relates to a device and a method for performing processes and/or reactions that are conducted in a temperature-controlled environment.

BACKGROUND OF THE INVENTION

A thermal cycler for implementing chemical and/or biological reactions comprising a body for accommodating one or more reaction vessels and a cover is disclosed, for example, in EP 1 013 342. Therein, the cover for closing the base body containing the reaction vessels is rigid and is placed on top of said body. In order to seal off the reaction vessels, an electrical positioner is actuated so that a moveable part of the rigid cover is pressed against the caps of the reaction vessels. The use of a rigid cover is suitable for a microtiter plate having identical reaction vessels with compressible caps. However, this rigid set-up is not suited to be adjusted in case reaction vessels (including caps) of different heights are present in the same array, for example due to manufacturing tolerances, since the pressure may not be evenly distributed over all wells or vessels. Also, the set-up as described in EP '342 may lead to uneven evaporation or condensation phenomena at the different reaction sites due to uneven (inhomogeneous) application of pressure, in particular at the fringe areas of the array.

A similar disclosure can be found in U.S. Pat. No. 5,475,610 comprising one embodiment (FIG. 19) according to which a rigid "platen" is displaced and pressed against an array of reaction vessels to keep said reaction vessels in position during thermocycling. The disclosure of U.S. '610 fails to teach how to balance potential differences in height and/or size of the reaction vessels since U.S. Pat. No. 5,475,610 preferably uses a rigid platen and exclusively deals with multiple well plates. The sample arrangement of U.S. '610 also does not take into account problems associated with an uneven pressure distribution caused by the rigid plate leading to uneven evaporation condensation effects at the lid. This holds in particular as the sealing principle of U.S. '610 relies on the presence of resiliently deformable caps. As another example of prior art, U.S. Pat. No. 6,703,236 relates to a device similar to U.S. '610 having similar features and, therefore, similar drawbacks.

WO 2006/002226 relates to a system for thermal cycling samples. The system comprises a thermal cycling device having a plurality of cavities adapted to receive at least a portion of a plurality of sample wells and a heated lid. The system of WO '226 further comprises at least one pneumatic driver connected to the heated lid. The pneumatic driver is configured to position the heated lid in a closed position and an open position, and to move the heated lid between the closed position and the open position. The system also comprises at least one pneumatic actuator connected to the pneumatic driver. The pneumatic actuator is configured to actuate the pneumatic driver to automatically position and move the heated lid between the closed position and the open position. The system also comprises at least one controller coupled to the pneumatic actuator. The controller configured to provide at least one of an electric signal and pneumatic signal to the pneumatic actuator to actuate the pneumatic driver. The teaching of WO '226, however, is restricted to a rigid heated lid and therefore leads to the very same problems in regard to uneven pressure distribution over the sample wells and therefore to (uneven) evaporation and condensation patterns, in particular at the fringes of the well plates.

WO 03/059517 discloses a method of applying a temporary seal to a reaction vessel for use in a water-bath thermocycler. Said temporary seal is achieved by placing a "sealing pad" against an operative surface of the reaction vessels and applying pressure to seal said pad against the operative surface of said vessels. WO '517 relates to a completely different basic design of thermal cyclers as the systems discussed above in that the system of WO '517 does not comprise a heated cover and that the plates are completely immersed in the temperature control medium. WO '517 also fails to address the problem of condensation and/or uneven evaporation and condensation at the fringes of the microtiter plates.

U.S. Pat. No. 6,518,060 relates to a "cover pad" used for covering a plurality of reaction wells open to the other surface and configured in a plate-shaped body provided for implementing chemical and/or microchemical reactions. Said cover pad is made of an elastomer comprising a soft backing which is provided with a rigid backing plate for stiffness. Due to the use of a rigid plate, the same problems arise in regard to condensation and evaporation in the lid area as discussed above.

In view of the prior art in the field, it is an object of the present invention to provide a device and a method according to which at least one sample, preferably contained in a vessel, is covered by means for covering in a manner so that potential evaporation of the sample or components of the sample is avoided or minimized and/or that condensation of vaporizable fluids of said sample on said means for covering and/or on the caps/lids of reaction vessels (if reaction vessels are used) and/or on the top part of sample wells (if multi-well plates or blocks are used) is minimized or avoided. In particular, inhomogenities in respect to evaporation and/or of condensation between different vessels/wells in an array of vessels or wells should be avoided/minimized. The latter applies in particular if a plurality of samples and/or vessels/wells is covered.

Furthermore, it is a preferred object according to the present invention to provide a device and a method that minimize or avoid to the damaging and/or deformation of reaction vessels and/or sample plates/blocks with wells during the process of covering the same. Preferably, such damage or deformation should be avoided/minimized if the reaction vessels and/or their caps and/or wells do not have the same height (tolerance).

SUMMARY OF INVENTION

These and other objects are solved by a device for controlling the temperature of at least one sample, wherein the device comprises at least the following components:

means for accommodating (2) at least one sample;

means for heating and/or cooling (4) at least one sample;

means for covering (3) at least one sample;

at least one force distribution unit suitable for (i) accommodating a force/pressure as exerted onto the force distribution unit by application of pressure and/or by at least one movable element (15, 15') that is part of the means for covering, and for (ii) redistributing and/or redirecting said force/pressure onto at least one sample and/or reaction vessel or sample plate or sample block.

In a preferred embodiment according to the present invention, the force distribution unit comprises at least one medium or material (10) that is unable to withstand a static shear stress and deforms continuously under the action of a shear force. In a preferred embodiment, this medium or material (10) is a gas, a liquid or a gel.

In a preferred embodiment, the at least one sample is contained in at least one (reaction) vessel or in at least one well or dimple or indentation of a plate or a block. Said vessel or plate or block can be disposable or can be an integral part of the device, in particular of the means for accommodating.

It is further preferred that said means for covering comprise at least one movable contact area (12) and at least one first means (30) for fixating said at least one movable contact area (12) in a defined position relative to the sample, wherein said first means (30) for fixating matingly engages with at least one second means for fixating (31).

The aforementioned objects are also solved by a process for controlling the temperature of the at least one sample, wherein said process comprises at least the following steps:

(a) placing at least one sample in at least one means for accommodating (2);

(b) covering the at least one sample in said means for accommodating with at least one means for covering (3);

(c) redistributing and/or redirecting a force/pressure as exerted onto a force distribution unit as situated between said means for covering (3) and the at least one sample by means of at least one medium or material (10) that is unable to withstand a static shear stress and deforms continuously under the action of a shear force and that is part of said force distribution unit.

In a preferred embodiment, step (b) comprises at least the following steps:

(b1) bringing a movable contact area (12) of a means for covering (3) in physical contact with at least one sample and/or at least one reaction vessel or plate or block containing said at least one sample;

(b2) fixating said movable contact area (12) of the means for covering (3) in the position achieved in step (b1) by means of engaging two matable means for fixating (30, 31);

(b3) applying a pressure/force onto the sample and/or reaction vessel(s), plate or block in addition to any potential pressure/force applied during the establishing of physical contact in step (b1), wherein said application of pressure/force occurs after having performed step (b2).

The present invention is preferably used for temperature sensitive chemical and biological reactions, preferably in conjunction with nucleic acid amplification, in particular assays based on polymerase chain reactions (PCR). The device of the present invention is particularly suitable as a thermal cycler. It is preferred that both the device and the process are used for thermally cycling at least one sample, preferably two or more samples.

The present invention thus relates to a device and a method for performing processes and/or reactions that are conducted in a temperature-controlled environment. While the present invention is exemplarily discussed in the context of thermal cyclers, the device and method of the invention are not restricted to this specific application but rather relate to all applications known to the person skilled in the art in which some kind of sample(s)/mixture(s) need(s) to be processed at a certain temperature.

In particular, the present invention relates to means for covering one or more sample(s) that are suitable to avoid or minimize evaporation and/or condensation of any vaporizable substance that may be present in the sample(s) or reaction mixture(s), in particular evaporation of substance at the fringes of a vessel or an array of vessels or condensation of said substance on the lid of a reaction vessel or a plate/block containing the sample(s) and/or the means for covering.

DETAILED DESCRIPTION OF THE INVENTION

Figure 1:
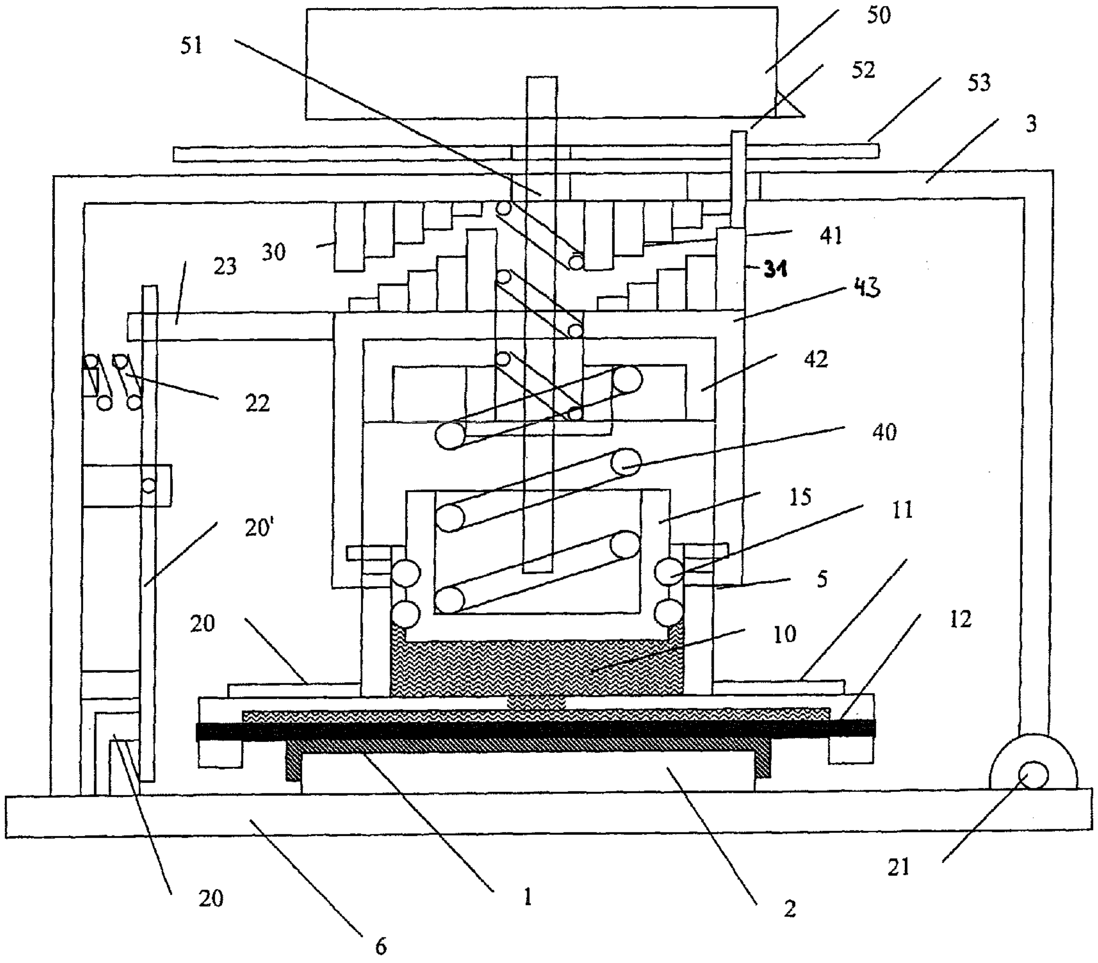
FIG. 1 is a schematic drawing of a device according to the present invention in a preferred embodiment wherein the force distribution unit comprises a fluid medium that redistributes pressure as exerted onto the force distribution unit by spring force onto a reaction vessel.

In accordance with the present invention, no restrictions exist in regard to the at least one sample. The sample can be a single substance, a reaction mixture or any other conceivable material. Blind samples are included.

In a preferred embodiment, the at least one sample is contained in at least on reaction vessel and/or in at least one well/dimple/indentation of a plate, in particular a sample well plate (multititer plate, PCR plate) or a block, in particular a flat block. The sample may also be contained in a consumable/disposable that is placed on a flat block.

The reaction vessel, plate or block can be disposable or can be a permanent and/or integral part of the device, in particular of the means for accommodating.

No restrictions exist in regard to the reaction vessels that optionally contain the at least one sample. In fact, it is a particular advantage of the present invention that different types of reaction vessels may be used and that even different reaction vessels can be used within the same set of experiments and/or can be contained in one array of the same means for accommodating. In particular, the present invention allows for reaction vessels of different height and/or height tolerances to be used in combination with each other. In case a plurality of reaction vessels is arrayed in a plate or a block or any other type of reaction vessel holder, the present invention not only allows for sites in the plate or block or reaction vessel holder to be empty (i.e. to not contain a reaction vessel)

but, in fact, provides means for covering that are particularly advantageous for such a setting.

The reaction vessels may be closed (i.e. may have a lid or cover or may be covered by a sheet or a film or foil) or may be open. According to the present invention, open reaction vessels can be used next to closed reaction vessels. Preferred reaction vessels are reaction tubes as known to the person skilled in the art as suitable for conducting PCR, including vessels having a flat bottom.

In a preferred embodiment, the reaction vessels, plates or blocks are sealed, for example, by means of caps (adding an additional height of approximately 1 to 2 mm to the overall height of the reaction vessel), in particular flat caps or domed caps or foils/films (having a thickness of approximately 0.02 mm).

In a preferred embodiment, the medium or material of the force distribution unit has a shear modulus of less than 1 GPa, preferably less than 0.5 GPa, preferably less than 0.1 GPa. A shear modulus of less than 0.001 GPa is further preferred. A medium or material for which the shear modulus cannot be reasonably determined because the material does not provide enough resistance to shear altogether is also preferred.

In case the viscosity of the medium or material can be determined, in particular in case said medium or material is a fluid or a gel, which is the preferred embodiment, viscosities at 25° C. of less than 1000 Pa·s, preferably less than 100 Pa·s preferably less than 10 Pa·s, further preferably less than 1 Pa·s are preferred, further preferably less than 0.1 Pa·s. Glycol is a presently preferably medium or material having a viscosity of less than 1 Pa·s.

It is furthermore preferred that the medium or material of the force distribution unit has a thermal conductivity of at least 0.1 $W \cdot m^{-1} \cdot K^{-1}$ at 293 K, further preferred at least 0.5 $W \cdot m^{-1} \cdot K^{-1}$.

Figure 2:
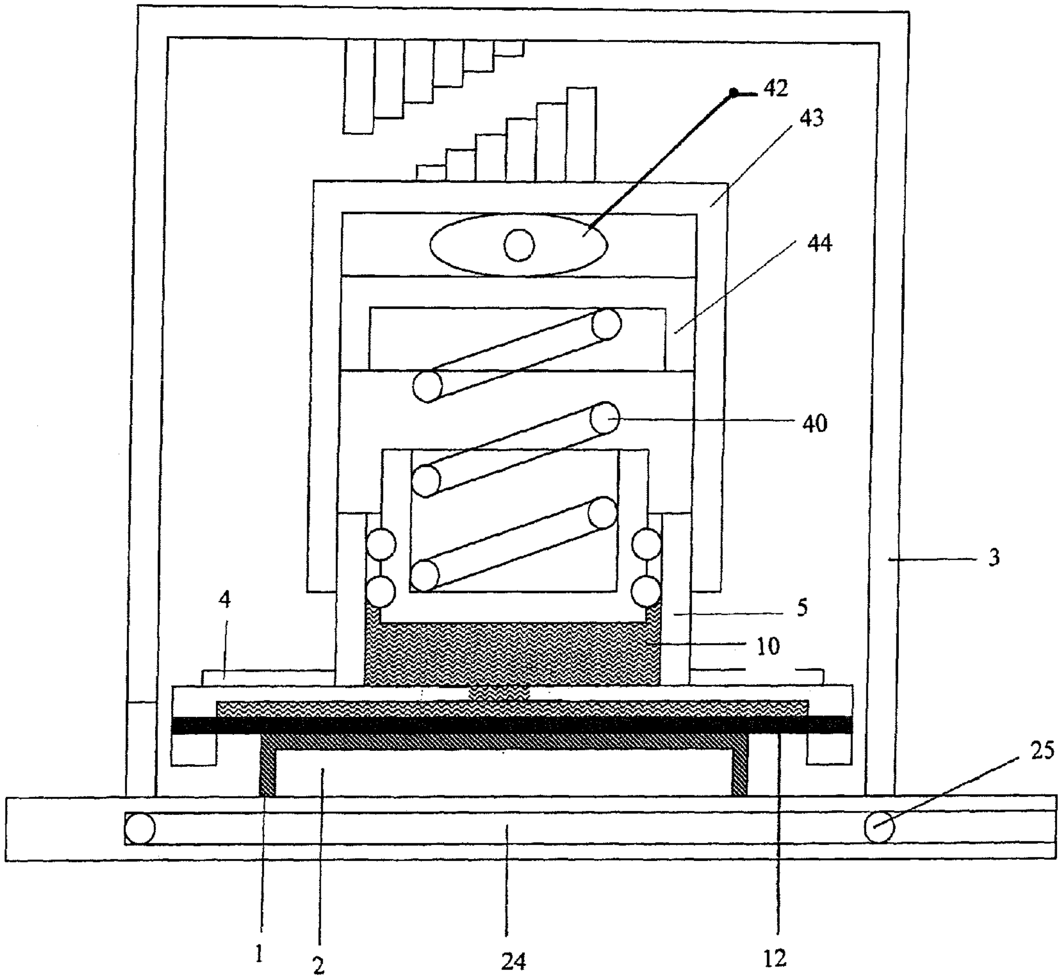
FIG. 2 shows an embodiment similar to the one shown in FIG. 1 comprising means for covering that move horizontally along a rail. Furthermore, the spring preloading device for adjusting the pressure as exerted onto the force distribution unit is realized as an excentric disk in this embodiment.

In a further preferred embodiment, said medium or material is a fluid, further preferred a gas or a liquid (cf. FIGS. 1 and 2). The term "liquid" is meant to comprise Newtonian and non-Newtonian liquids, sols and gels, dispersions and suspensions, as well as any mixture of two or more of the aforementioned substances. The medium or material according to the present invention can also be an assembly of solid particles that freely flow against each other under shear, for example as is the case for sand or an assembly of beads.

In the context of the present invention, the term "force distribution" is meant to be used in an equivalent manner with the term "pressure distribution" (pressure=force/area).

In a further preferred embodiment of the present invention, the medium or material of the force distribution unit is contained within a containment that may at least partly change shape in accordance with a change in the shape of the medium material (i.e. is deformable) and is capable to contain the medium or material during said change of shape. In a preferred embodiment, the containment comprises more than one type of material, wherein at least one material of said plurality of different materials must be deformable by the medium or material contained within the containment. Preferably, the containment comprises at least one deformable contact area (12).

Figure 3A:
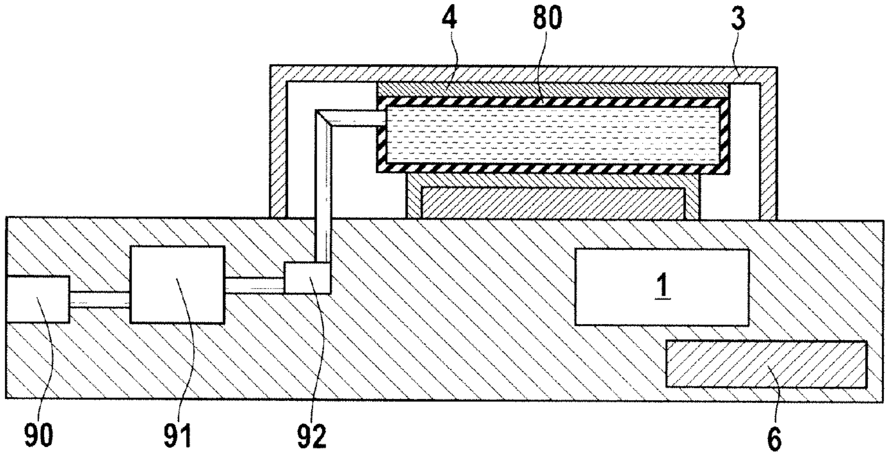
FIG. 3 shows another preferred embodiment according to the present invention using a containment filled with a liquid or a gel and having at least one deformable contact area as the force distribution unit. The containment may optionally be connected to a pressure management system comprising a compressor, a pressure sensor and a valve.

In a preferred embodiment, a fluid, preferably a gel, is contained in a pad made of a deformable material, preferably an elastic or deformable plastic or polymer material (cf. FIG. 3*a*).

In another preferred embodiment, a fluid is contained inside a containment comprising a rigid frame and at least one outer flexible and/or deformable contact area. In this embodiment, it is preferred that the rigid frame comprises a connection or a conduit for applying pressure onto the fluid inside the containment from outside of the containment. The containment preferably also comprises an array of elevated areas that are closer to the contact area than other parts of the containment and that are able to define channels for the fluid inside the containment (cf. FIG. 4).

It is further preferred that the containment, in particular the containment comprising a deformable contact area as described above, is coated, in particular on the side that is in contact with the sample and/or the reaction vessel(s). Coatings that minimize adhesion of the containment in regard to the sample(s) or reaction vessel(s) and/or improve stability or abrasion properties are preferred. Coatings may be blackened to lead to improved reflectivity properties. In a preferred embodiment, the coating renders the contact area resilient against puncture and other mechanical damage. A metal or a teflon coating is preferred. Coatings that enhance thermal contact and/or improve thermal stability are particularly preferred.

In a preferred embodiment, the liquid/gel as the medium or material within a deformable containment is preferably connected to a pressurizing unit, preferably a compressor and/or a pump, which is further preferably connected to a valve and/or a pressure sensing unit. In this embodiment, the pressure as exerted by the pad can be regulated and controlled (cf. FIG. 3*a*). In an alternate embodiment, the deformable containment is realized as a flexible tube and the medium of the pressure distribution unit is a fluid. The flexible tube preferably exerts force/pressure onto a frame placed on top of the reaction vessels (cf. FIG. 3*b*).

In an alternate embodiment, pressure can be exerted by means of directly or indirectly compressing the fluid inside a containment, wherein said containment has at least one deformable contact area. Direct compression is achieved by directly mechanically pressing onto a deformable area of the containment, preferably by means of a mechanical or a motorized actuator. Indirect compression may be mediated by means of compressing the medium or material, possibly outside or from the outside of the containment.

No restrictions exist in regard to the means for heating and/or cooling. Preferably, the means are capable of heating or cooling at least one sample and/or at least one reaction vessel or plate or block. It is preferred that the means for heating and/or cooling are selected from the group of resistance heater, fluid mediated heating/cooling, air/gas cooling, Peltier heating/cooling, friction (Joule) heating/cooling, and/or radiation heating.

In a preferred embodiment according to the present invention, at least one means for heating and/or cooling at least one sample and/or reaction vessel is part of the means for covering. In this case, it is preferred that said means for heating and/or cooling minimizes or avoids evaporation of sample and/or minimizes or avoids condensation of vaporized sample on or in the vicinity of the means for covering.

It is further preferred, that an (additional) means for heating and/or cooling is provided in the means for accommodating a plurality of samples and/or reaction vessels.

In a further preferred embodiment, means for heating and/or cooling are provided as a part of the force distribution unit, in particular in conjunction with the medium or material that deforms continuously under the action of a shear force. In this context, it is particularly preferred that said medium or material is a fluid, in particular a gel or a liquid. It is further preferred, that the gel or the liquid has a high thermal conductivity (at least 0.1 $W \cdot m^{-1} \cdot K^{-1}$). It is further preferred that the liquid or the gel is in contact with a heat exchanger unit in order to change the temperature of the liquid/gel as it is brought in contact with the sample(s) and/or the reaction vessel(s). Preferably, such heat exchanger is a heating plug or a heating sheet.

No restrictions exist in regard to the means for accommodating at least one sample. This means may be a holder for reaction vessels or may be a block or a plate, for example a (flat) block made of metal, plastic materials or of composite materials that may comprise wells or dimples or any other type of indentation/containment.

The means for accommodating may be, for example, a (microtiter) plate, a water bath with an insert for holding reaction vessels, a carousel, any other type of multi-well plate or a flat block. Preferably, the means for accommodating are block- or box-shaped. It is preferred that said means are thermally insulated. It is further preferred that the means for accommodating comprise means for heating and/or cooling the reaction vessel(s) and/or the sample(s) from below and/or from the side.

The means for accommodating may be disposable or may be reusable. They may temporarily or permanently be part of a base body, or of any other part of the device according to the present invention.

No restrictions exist in regard to the means for covering at least one sample or at least one reaction vessel or the plate/block. The means for covering are preferably temporarily or permanently affixed to and/or aligned with the means for accommodating the sample(s) or reaction vessel(s). In this context, it is preferred that means for covering and the means for accommodating share a common base body. Further preferably, the unit comprising means for accommodating and the means for covering (optionally comprising a base body) completely enclose and/or encase the at least one sample or reaction vessel. Complete enclosing and/or encasing improves temperature stability.

In a preferred embodiment according to the present invention, the means for covering at least one sample or reaction vessel are in physical and thermal contact with at least one force distribution unit, wherein said force distribution unit is suitable to bring the at least one sample or reaction vessel in thermal contact with the means for covering and thereby establishes (direct) thermal contact between the force distribution unit and the sample(s) thus allowing efficient heating and/or cooling of the at least one sample. Tight mechanical and thermal contact between the sample and/or the reaction vessel, in particular the top thereof and/or the cover of the reaction vessel, on the one hand, and the force distribution unit (being part of the means for covering) on the other hand, is preferred for stable and efficient thermal processing of the chemical or biological process.

No restrictions exist in regard to the force distribution unit except that said unit must be suitable to (i) accommodate a force/pressure as exerted onto the unit by application of pressure and/or by means of moving a movable part that is preferably a part of the means for covering and to (ii) redistribute and/or redirect said force/pressure onto at least one sample contained in a means for accommodating. Preferably, the force distribution unit comprises at least one medium or material that is unable to withstand a static shear stress and preferably deforms continuously under the action of the shear force.

In a preferred embodiment, pressure is exerted onto the force distribution unit (and redirected onto the reaction vessel) by simply closing and/or locking the means for covering (in their final position). In another preferred embodiment, pressure is exerted, additionally or exclusively, by means of moving a movable part of the means for covering in addition to or during to the process step of closing and/or locking the means for covering. In yet another embodiment, pressure is exerted by means of pressurizing the medium or material of the force distribution unit.

Figure 4:
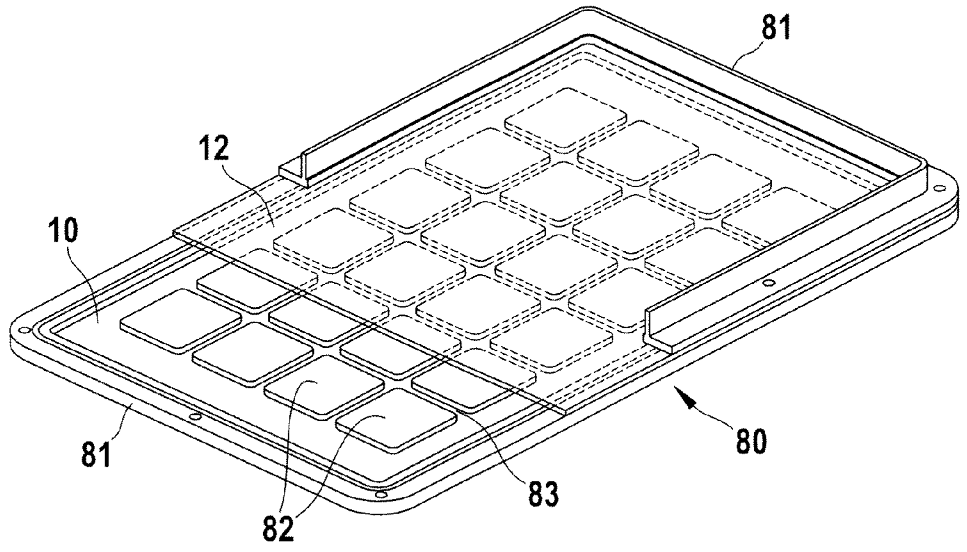
FIG. 4 shows a preferred realization of a containment for the material or medium of the fluid distribution unit comprising a fluid, an array of elevated areas for better thermal contact and an outer, deformable contact area.

In a preferred embodiment according to the present invention, the force distribution unit is realized as a containment (80) that comprises at least one deformable contact area (12) and at least one rigid frame (81). In this preferred embodiment (as illustrated in FIG. 4), the containment (80) comprises at least one medium or material (10) that is unable to withstand a static shear stress and deforms continuously under the action of a shear force. Preferably, this medium or material is a liquid that is, further preferably, at least partly incompressible.

It is further preferred, that the medium or material (10) inside said containment (80) is in fluid communication with a reservoir (not shown in FIG. 4) for said medium or material, preferably by means of a conduit that is further preferably flexible (not shown in FIG. 4). Said reservoir preferably also contains the medium or material (10) and is itself at least partly deformable. Said reservoir may be (de)compressed by means of applying a force or a pressure. Preferably, said reservoir is realized as a bellows system. Said bellows may be (de)compressed by means of direct application of force or by means of applying force as mediated by a spring.

In this context, it is further preferred that the containment (80) comprises an array of elevated areas (82) that (i) are located inside the containment and can be brought in physical and thermal contact with the deformable contact area (12) of the containment (80), for example by means of removing medium or material (10) out of the containment (80), for example by decompressing the bellows of the reservoir (i.e. creating an "under-pressure").

Furthermore, in a preferred embodiment, said elevated areas (82) create a system of channels (83) for the medium or material (10), preferably the fluid. These channels form underneath the deformable contact area (12).

This preferred embodiment allows to apply pressure onto the reaction vessels independent of the actual number of reaction vessels in the means for accommodating and/or independent of the force applied.

The containment (80) of the preferred embodiment as described above is preferably used in a process for covering an array of more than one reaction vessels, which are preferably placed at varying distances in respect to each other and/or which are arranged within a holder for reaction vessels (means for accommodating) that could hold more reaction vessels, i.e. that has empty sites for reaction vessels. In such a process the force as applied by the force distribution unit depends on the number and/or arrangement of reaction vessels. Also, in order to allow for a controlled heating and/or cooling of the reaction vessels, thereby avoiding or minimizing evaporating and/or condensation in the upper part of the reaction vessels, a defined thickness of the fluid medium or material (10) of the containment (80) is desirable. In fact, in order to minimize response time based on heat capacity, the thickness of the layer of fluid medium or material inside the containment should be, preferably, as small as possible and as defined as possible in order to achieve as homogenous as possible a temperature profile in the x-y-plane of the contact area (12) of the containment (80).

The process for controlling the temperature of an array of reaction vessels (1) as described above preferably comprises the following steps:

In a step (a), the pressure of the medium or material (10) inside said containment (80) is lowered so that a deformable contact area (12) of the containment is brought in physical contact with an array of elevated areas (82) which are located inside said containment (80) and behind said deformable contact area (12) (as seen from the perspective of the reaction vessels that are brought in contact with said contact area). In a preferred embodiment, the medium or material is a fluid that is removed from the containment (80) by means of applying an "under-pressure" in the above-mentioned reservoir, preferably realized as a bellows system. For example, "under-pressure" is achieved by expanding the bellows, preferably mediated by means of a spring.

In a second step (b), the deformable contact area (12) is being brought into physical contact with the reaction vessels and the pressure of medium or material (10) in the containment (80) is increased so that the deformable contact area (12) is brought in thermal and/or physical contact with all reaction vessels and at least a thin film of the medium or material (10) is formed between the elevated areas (82) and the deformable contact area (12).

No restrictions exist in regard to the movable element of the means for covering except that said movable part must be able to exert a force/pressure onto the force distribution unit. According to a preferred embodiment of the present invention, the movable element is a piston (5) operated hydraulically and/or pneumatically. The control of the piston is preferably achieved electronically in an automated or semi-automated manner. Force/pressure may also be exerted by means of a knob that can be turned, either by hand or by means of an electrical motor. A manually and/or electrically operated actuator and/or spindle is also preferred in case such an embodiment is chosen.

According to an alternative embodiment of the present invention, force/pressure may also be exerted by application of pressure onto the force distribution unit, i.e. not by way of moving the means for covering and/or a movable part thereof. It is preferred, in this case, that the medium or material of the force distribution unit is at least partially incompressible, for example a liquid. According to one embodiment, the medium is a gas and pressure is exerted by means of a compressor and/or pump and is/are preferably controlled by means of a pressure sensor. Alternatively, a (partly) incompressible liquid may be exposed to compression forces.

Either embodiment, application of pressure and/or application of force by means of a movable element will cause the medium or material of the force distribution unit to deform continuously under the action of the shear force (pressure) as applied. Therefore, the medium or material will redistribute itself as evenly as possible depending on the specific geometry (in particular specific height differences) of the sample(s) as optionally contained in wells or in reaction vessel(s). This results in an even and homogeneous distribution of pressure onto the samples, in particular onto reaction vessels, wells and/or lids. Therefore, heat can be exchanged in an even and homogeneous manner and, specifically, potential evaporation and/or condensation in the vicinity of the force distribution unit can be controlled in as homogeneous a manner as possible. Such a redistribution and/or redirection of force/pressure is not possible with embodiments known from the prior art according to which the reaction vessels are held in place by means of a material that is able to withstand a static shear stress and does not continuously deform under the action of a shear force, i.e. keeps shape while exposed being to an outside force or pressure. This disadvantage of the embodiments known in the art holds in particular if this medium or material for pressure/force redirection is a rigid plate. Such a rigid plate may deform under pressure thus decreasing the pressure in particular at the fringes of the plate. Evaporation at the fringes and/or uneven condensation may be the consequence of this deformation.

According to a further preferred embodiment of the present invention, an additional sheet or film or foil may be positioned in between the above-described force distribution unit and the sample(s) and/or reaction vessel(s). Preferably, said sheet is flexible and can accommodate the deformation of the medium or material of the force distribution unit. Further preferably, said sheet is tight, in particular fluid-tight, in regard to the sample material. It is further preferred that said sheet is made of a material that is cheap and can be easily replaced. This is particularly preferred in case the samples or reaction vessels are open and therefore need to be sealed against the force distribution unit by means of said sheet. In order to avoid (cross-)contamination between different materials, said sheet is preferably discarded after every use. This also protects the force distribution unit and/or the means for covering the at least one sample from the content of the (open) samples or reaction vessels.

No restrictions exist in regard to the means for fixating. It is preferred that the means for fixating (30, 31) are capable of fixating the contact area in a plurality of different positions relative to a potential sample (preferably contained within a reaction vessel/block or plate), wherein said plurality of positions are preferably continuously accessible.

In a preferred embodiment, the means for covering (3) comprises at least one unlocking device (65) for disengaging at least the first and second means for fixating.

In a preferred embodiment, said defined position is the vertical z-direction, i.e. the movable contact area can be fixated (or locked) in z-direction, further preferably in positive z-direction. The positive z-direction is essentially perpendicular to the sample surface and points away from said sample surface. It is preferred that movement in the opposite direction, i.e. in particular in negative z-direction, is essentially unaffected by said fixation/locking in the (opposite) positive z-direction.

In respect to step (b) using said means for fixating, it is preferred that said initial pressure/force as exerted onto the reaction vessel(s) after the two matable means for fixating have engaged, i.e. after step (b2) but before step (b3), is zero or close to zero or is given by the weight of the means for covering and is, at any rate, smaller than the final pressure/force as ultimately established after fixating the movable contact area. Furthermore, it is preferred that the weight of the means for covering—or a part thereof—is sufficient to enable any movement of the contact area that is required to establish physical contact between the contact area and the sample or vessel/plate/block, i.e. to perform step (b1).

In a further preferred embodiment according to the present invention, at least one of the two means for fixating is movable, preferably in one direction only, relative to the corresponding matable second means for fixating. The second means for fixating is preferably connected to the means for covering. It is preferred that said second means for fixating is not moved (i.e. remains stationary) during the process of closing the means for covering. Alternatively, the second means for fixating is moved in the above-described manner while the first means for fixating remains stationary.

Preferably, the type of movement of the at least two means for fixating relative to each other during the process of fixating [i.e. during step (b1)] is selected from a linear or from a circular movement or from any combination of two or more of these movements.

In a preferred embodiment, the two means for fixating matingly engage by means of fitting geometries and/or by means of frictional engagement.

In one preferred embodiment, the at least two matable means for fixating are realized as two matable height adjustment contours which preferably have the contour of a sequence of a plurality of steps with an increasing step height or the contour of an increasing ramp, preferably a linearly increasing ramp (see FIG. 1).

Figure 6:
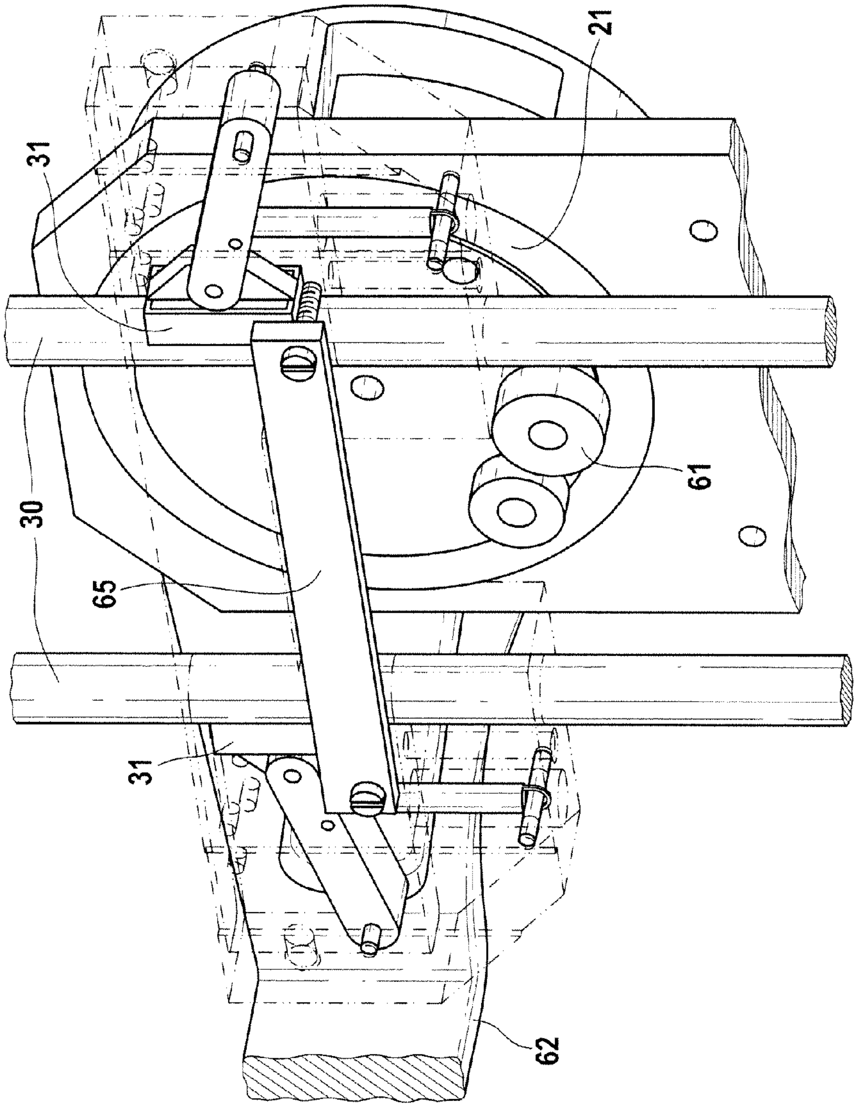
FIG. 6 shows another preferred embodiment according to the present invention in which the means for fixating (30, 31) are realized as a frictional catch.

In another preferred embodiment, the two matable means for fixating are realized as a frictional catch ("Reibgesperre") (see FIG. 6). A "frictional catch" in the meaning of the present invention is any means for fixating that temporarily hinders a movable element, preferably the contact area (12), in respect to at least one possible movement in at least one direction. Technical realizations of means for fixating as described in Chapter 9 ("*Gehemme und Gesperre*") of "*Konstruktionselemente der Feinmechanik*" (Ed.: Werner Krause; ISBN: 3-341-00461-0), pages 445-460 are hereby incorporated by reference.

In a preferred embodiment of the inventive process as described above, step (b2) is conducted so that the movable contact area is fixated only in respect to the movement performed in step (b1), preferably in positive vertical z-direction.

In one preferred embodiment in respect to step (b3), at least one movable element (15) of the means for covering is used, after step (b2), to exert a force/pressure onto the sample(s) and/or reaction vessel(s) or plate/block in step (b3) by means of moving the movable element (15) towards the sample(s) or reaction vessel(s) or plate/block, preferably in negative z-direction.

In another preferred embodiment in respect to step (b3), the movable contact area (12) is deformable and is part of a containment that contains a fluid material or medium, the hydraulic pressure of which is increased so that the contact area (12) exerts (an additional) force/pressure onto the sample and/or reaction vessel or block or plate.

In a preferred embodiment, steps (b2) and (b3) can be coupled so that step (b3) immediately and/or continuously follows step (b2). In a preferred embodiment, steps (b1), (b2) and (b3) are integrated in one single continuous movement of the means for covering (3) in one direction. Preferably, said movement in one direction is linear or circular and further preferably involves the movement of at least one part of the means for covering around at least one bearing and/or by at least one pin or pivot point.

Preferably, the fixating as achieved in step (b2) establishes a counterforce (reactio) to any force/pressure (actio) as applied onto the sample/reaction vessel/plate/block in step (b3).

In a preferred process for opening the means for covering (after having closed them), first the pressure/force exerted onto the reaction vessel(s) by means of the movable element (15) or the movable deformable contact area as described above is reduced and/or removed and subsequently the matable means for fixating (30, 31) are disengaged, i.e. steps (b2) and (b3) are reversed, preferably by means of an unlocking device (65) as described above.

Only after these steps, the means for covering are removed, opened or brought out of alignment with the sample, i.e. step (b1) is reversed.

Among the many advantages of using means for fixating (30, 31) are the following: (i) pressure/force does not need to be exerted directly onto the sample by means of moving an electrical or pneumatic actuator. Rather, force/pressure can be applied onto the sample by means of having all physical units in place and increasing the pressure of a (hydraulic) medium inside a containment and taking advantage of the counterforce (reactio) created by the means for fixating; (ii) the application of (hydraulic) pressure onto the sample (and/or any actuation of any movable element if used) is not required until the sample is in physical contact with a contact area of the means for covering; thereby, "idle" application of pressure or actuation is avoided or minimized; (iii) as already mentioned above, the device and the method of the present invention allow to use reaction vessels/plates/blocks of different height while the pressure/force as applied upon closing the means for covering is always the same or similar; (iv) the force/pressure necessary to ultimately seal the contact area against the sample or vessel/plate/block can be applied at any position of the sample or vessel/plate/block since the means for fixating the contact area relative to the sample can be fixated in a continuous manner only dependent on the height of the vessel/plate/block; (v) in order to perform steps (b1) to (b3) of the process according to the present invention, it is sufficient (although by no means required) to establish one continuous movement of the means for covering around one bearing or pin or pivot; (vi) all of the above can be achieved while evaporation and/or condensation of components of the sample is/are minimized or avoided.

A particular advantage and synergetic effect can be seen in combining the force distribution unit as described above with the possibility of using means for fixating (30, 31) as described above to establish fixation of the deformable contact area (12) in physical contact with the sample (1) and/or reaction vessel/plate/block as said fixation "redirects" any pressure/force built up by the medium or material (10) of the force distribution unit onto the sample and/or reaction vessel/plate/block ("reactio") thus establishing firm contact between the means for covering (3) and the sample and/or reaction vessel/plate/block without moving any actuators or other movable mechanical parts of the force distribution unit.

DETAILED DESCRIPTION OF THE FIGURES

A preferred embodiment according to the present invention is illustrated in FIG. 1. Therein, a base body (6) supports means for accommodating (2) realized as a block supporting, in this case, a (multi-well) plate (1).

According to the embodiment shown in FIG. 1, the means for covering (3) are realized as a box-shaped lid that is connected to the base body (6) by means of pivoting means (21) realized as a hinge. The lid can be fixated and aligned in respect to the base body by means of a locking mechanism (20, 20'). In this specific embodiment, the locking mechanism comprises a hook (20') engaging with a corresponding protrusion (20) as attached to the base body (6). Unlocking of said locking mechanism is achieved by means of a spring (22) in conjunction with a unlocking actuator (excenter) (23).

By way of closing, a movable element of the means for covering, here realized as a shaft (51) being engaged with a spring preloading device (42) for spring (40) exerts pressure onto the force distribution unit (5, 10, 11, 15 and 12). The specific pressure can be adjusted by means of the device (42) being able to engage with the shaft (51) connected to a turning knob (50). In this preferred embodiment, the movable element of the means for covering also comprises a spring (41) that is of weaker spring force than spring (40) and allows to lower the movable element in a more controlled manner. The pressure as exerted onto the force distribution unit by means of turning the turning knob (50) may be actuated manually or electronically.

In the preferred embodiment as shown, the force distribution unit comprises a fluid that is the medium or the material (10). Said fluid is contained by a cylindrical vessel (5) that is sealed against the piston (15) with sealing means (11) and against the reaction vessel (1) by means of the deformable contact area (12).

Therefore, upon closing the lid (3) and/or by actuating the turning knob, pressure may be exerted onto the plate by means of the fluid (10) of the force distribution unit. The fact that the fluid has no shear force and the contact area (12) is deformable allows to evenly distribute the force as exerted onto a comparatively small area by means of cylinder (15) over the entire area of the plate (1).

The height of the contact area (12) relative to the sample plate (1) can be fixated [in accordance with step (b2)] in the position of the closed means for covering (3) as shown in FIG. 1 by two engaging height adjustment contours (30) and (31) as the matable means for fixating. As only a cross-section is shown, the matable height adjustment contours must be visualized as arranged like a "spiral case" along the circumference of a circle. Therefore, by turning knob (50) being connected to (43) via (42), no force is applied onto the sample/plate (1) until the two "spiral cases" matingly engage. During this turning of the knob, the horizontal surfaces of (42) and (43) are in physical contact (as shown in FIG. 1). Once the means for fixating matingly engage and fixate any movement of (43) in positive z-direction, any further turning of knob (50) will lead to a relative vertical movement of (42) away from (43) and, therefore, to the loss of physical contact between the horizontal surfaces of (43) and (42). In this case, turning the knob (50) now will exert a force/pressure onto the sample (1) as mediated by the spring (40).

In the position shown in FIG. 1, first height adjustment contour (30) is connected to the cover (3) and has not yet been moved into mating engagement with the second height adjustment contour (31) that is connected with the connecting frame (43). In this embodiment, contour (31) comprises a pointer (52) that is used in conjunction with a scale (53) to control and/or adjust the position.

An alternative preferred embodiment as shown in FIG. 2 essentially corresponds to the embodiment shown in FIG. 1 with the following notable exceptions. First, the lid (means for covering) (3) is not aligned in respect to the base body by means of a hinge and a locking mechanism but rather by means of a movable rail member (25) attached to the lid (3) that can move freely in one direction on a rail (24). In this preferred embodiment, no locking mechanism is present and the final position of the slidable lid is determined by the end of travel of the rail (24).

In another difference to FIG. 1, the preloading of the spring (40) exerting the pressure on the force distribution unit and therefore the overall pressure as ultimately applied onto the sample plate (1) is achieved by means of an excentric disc (42), preferably an oval one, that can be actuated by hand or electronically. The force as exerted by means of the excentric disc (42) is not directly applied onto spring (40) but rather by means of the spring preloading device mediating means (44) realized as a pressure piston.

In another alternative embodiment that is preferred in the context of the present invention, FIG. 3*a* shows a containment (80) as the force distribution unit that consists of a deformable but fluid-tight material that contains a fluid medium or material. This containment (80) accepts and redistributes the force as applied by means pressurizing the fluid material or medium inside. In this embodiment, a resistance heater as the means for heating and/or cooling (4) is arranged on top of the force distribution unit.

The force distribution unit is preferably realized as a containment that comprises a compressible fluid, which is in fluidic contact with a compressor (90) that allows to change the pressure inside the pad and therefore the pressure as exerted onto the reaction plate (1). Correspondingly, the device of FIG. 3*a* does not need or comprise a movable plate or piston (15) for exerting the pressure. In the embodiment shown in FIG. 3*a*, a compressor (or pump) (90) is connected to a valve (92) and a pressure sensor (91). Both means for covering (3) and the plate (1) contained in the means for accommodating are supported by a common base body (6).

Figure 3B:
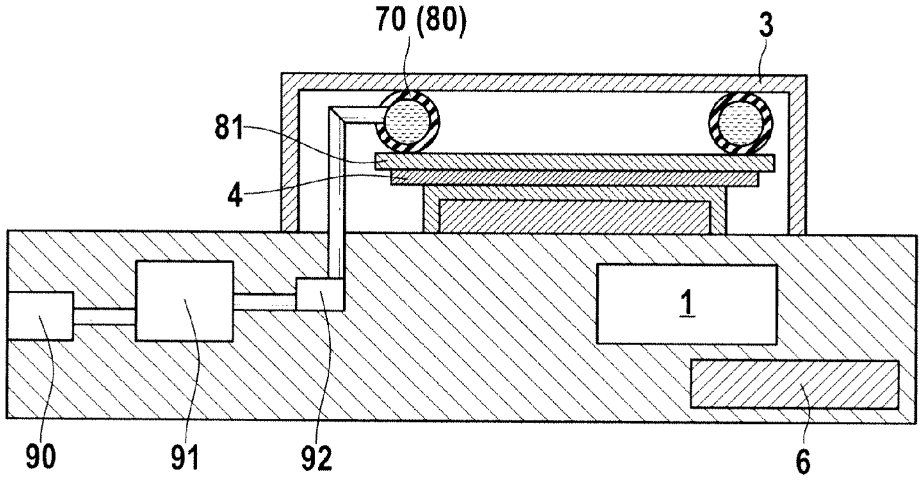

FIG. 3*b* shows an embodiment similar to the embodiment shown in FIG. 3*a*, with the notable difference that the force distribution unit is realized as a flexible tube (70) that is in contact with a compressor/pump (90). A frame (81) mediates the pressure as exerted by the pressurized flexible tube (70). The means for heating and/or cooling (4) are realized as a resistance heater.

FIG. 4 as already described in detail above shows a containment (80) suitable as a force distribution unit. Said containment (80) comprises a rigid frame (81), a deformable contact area (12) (preferably made of viton) and elevated areas (82) inside the containment (80) and underneath contact area (12). An array of areas (82) preferably forms a system of channels (83) for fluid distribution inside the containment.

The embodiment as shown in FIG. 5 essentially corresponds to the embodiment shown in FIG. 2 and highlights the sequence of steps that lead to a firm closing of the cover (3)/contact area (12) onto the sample.

Figure 5A:
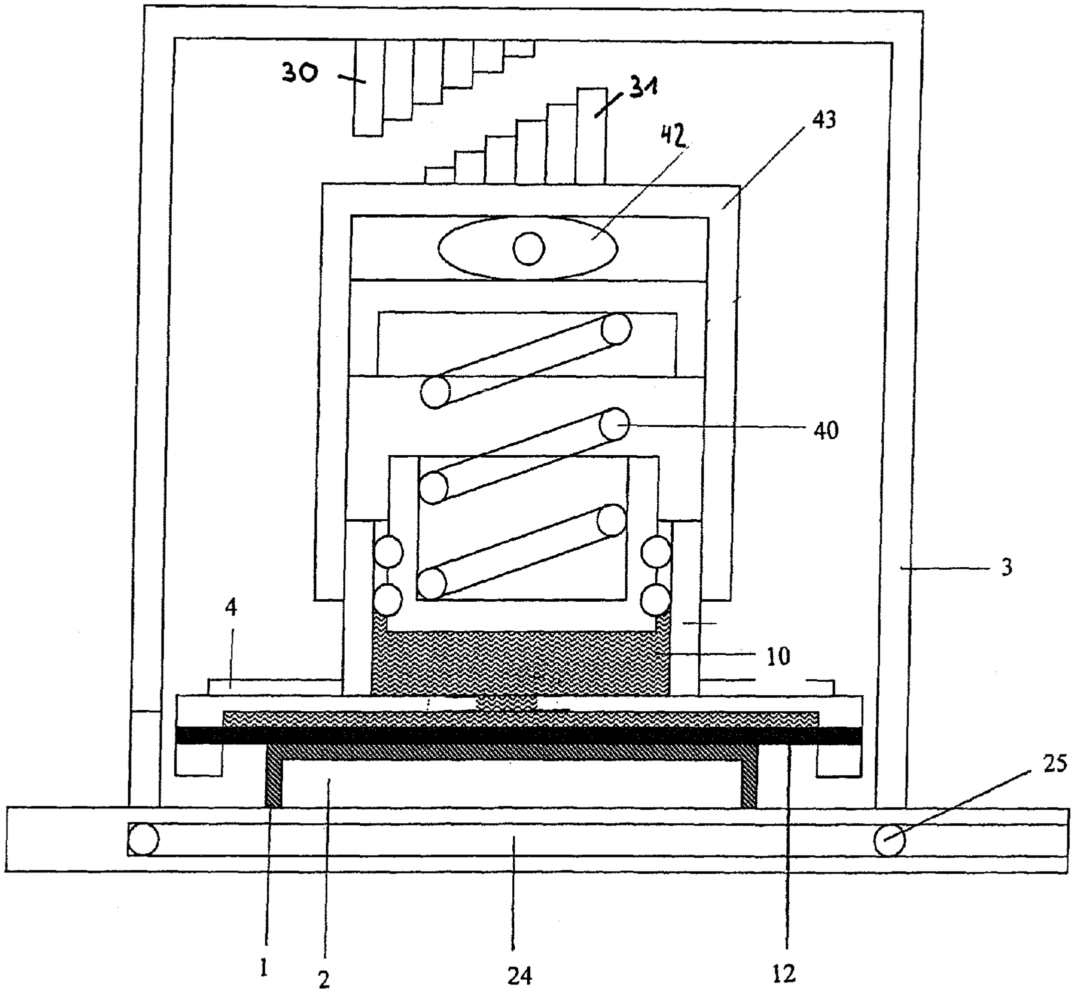
FIG. 5 shows, in a sequence of steps, how first and second height adjustment contours (30, 31) engage, fixate and how afterwards a predetermined pressure is exerted onto the reaction plate/sample.

FIG. 5A shows the position in which the cover/lid (3) is in its final position, aligned with the means for accommodating (2) and the reaction plate (1) by means of the rail member (25) being at the end of travel of rail (24). In this position, the movable contact area (12) has been lowered onto reaction plate (1). In this position, height adjustment contours (30) and (31) do not engage and, consequently, the contact area (12) is not fixated in positive z-direction [step (b1) as described above].

Figure 5B:
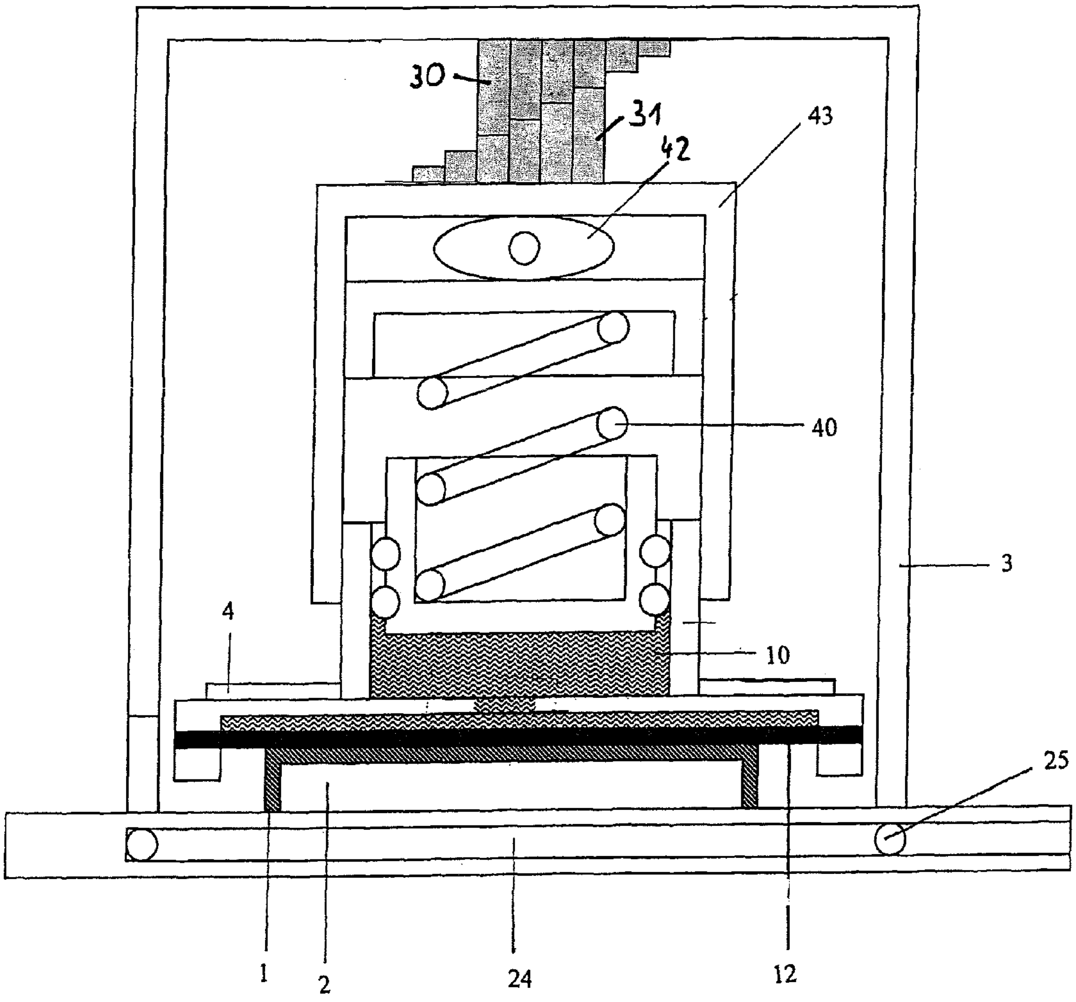

FIG. 5B shows how the height adjustment contours are mutually engaged by means of moving the first height adjustment contour (31) into frictional engagement with the second height adjustment contour (30). This engagement fixates the contact area (12) in positive z-direction, i.e. any pressure exerted by disk (42) is (re)directed onto the reaction plate. The number of steps of the step-shaped height adjustment contour (here: four steps) that engage are determined by the height of sample plate (1). This fixating step is in accordance with step (b2) as described above.

Figure 5C:
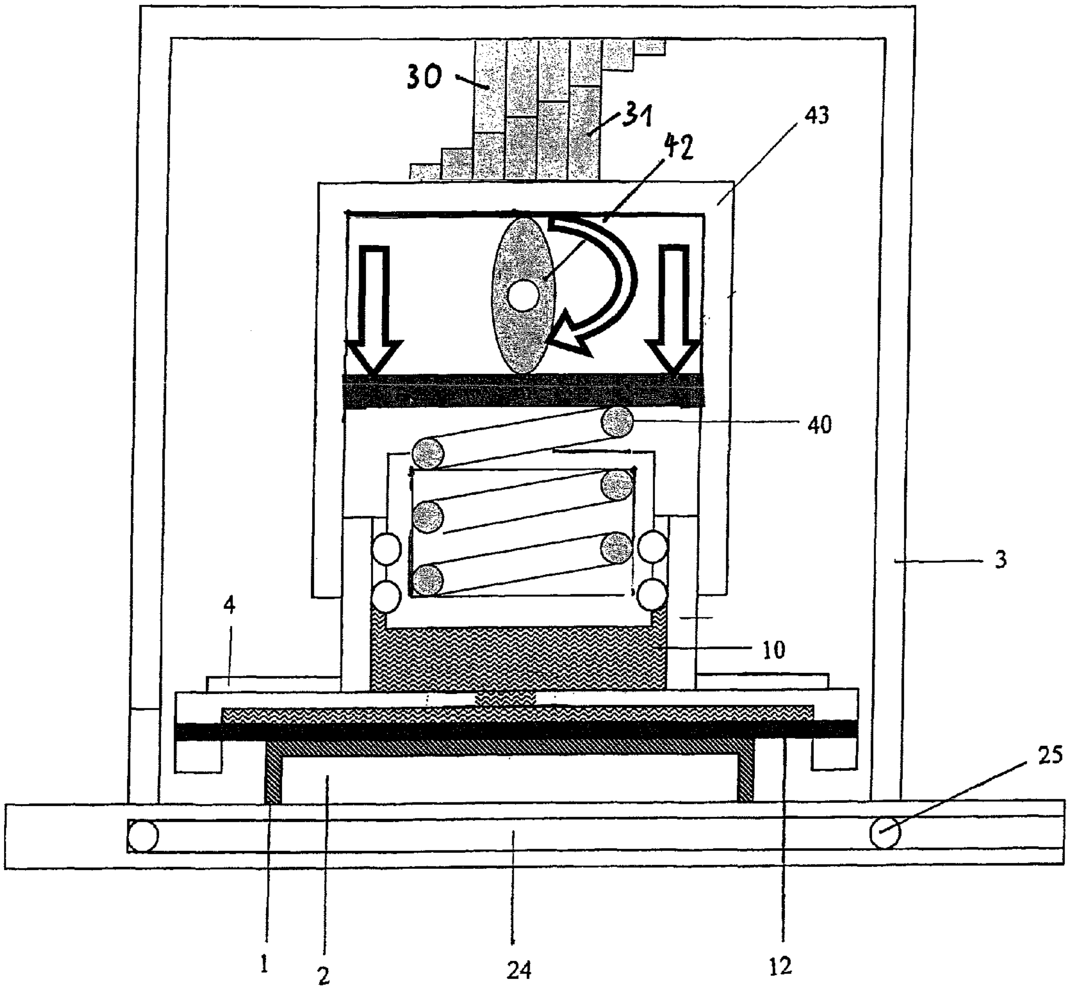

FIG. 5C shows how (additional) pressure is exerted onto the reaction plate (1) in a last step (b3) by means of turning eccentric disc (42) thereby increasing the force as exerted by means of spring (40). The height adjustment contours (means for fixating) remain unchanged in their respective positions in this step.

FIG. 6 shows an alternate embodiment in which the means for fixating (30) and (31) are realized as a frictional catch. Therein, contact area (12) (not shown) is lowered along rods (30) by means of closing the means for covering (not shown) as connected to handle lever (62). The lever (62) pivots around disc (21). A pin (61) is connected to said disc and engages or disengages the brake shoe (31) depending on the position on the lever (62), i.e. the position of the cover (closing or opening).

Once the physical contact between contact area and sample is established, brake shoe (31) frictionally engages with rod (30) thus blocking the positive z-direction, i.e. any upward movement along rod (30).

For unlocking, the movement of the lever (62) is reversed, bringing pin (61) in contact with unlocking bar (65) thus disengaging the brake shoe (31) from the rod (30) and freeing the positive z-direction.

All publications, patents and patent applications cited in this specification are herein expressly incorporated by reference to the same extent as if each individual publication, patent or application was specifically and individually indicated to be incorporated by reference.

The invention now being fully described, it will be apparent to one of ordinary skill in the art that many changes and modifications can be made thereto without departing from the spirit or scope of the appended claims.

REFERENCE SIGNS

Cover for Sample with Homogeneous Pressure Application

1 reaction vessel(s) or plate (sample)
2 means for accommodating
3 means for covering
4 means for heating and/or cooling
5 movable element of means for covering
6 base body
10 medium or material of force distribution unit/containment
11 sealing means
12 movable and/or deformable contact area
15, 15' movable element of means for covering (piston)
20, 20' locking mechanism for means for covering
21 pivoting means
22, 23 unlocking mechanism for means for covering
24 rail
25 movable rail member
30 first means for fixating
31 second means for fixating
40, 41 springs
42 spring (pre-)loading device
43 connecting frame
44 spring preloading device mediating means
50 turning device/knob
51 shaft (actuator)
52 pointer
53 scale
61 pin
62 lever (handle)
65 unlocking device
70 flexible tube
80 containment (for medium or material of force distribution unit)
81 rigid frame
82 elevated area
83 channel
90 pump/compressor
91 pressure sensing unit
92 valve

The invention claimed is:

1. A device for controlling a temperature of at least one sample, wherein the device comprises at least the following components:

at least one means for accommodating the at least one sample;

at least one means for heating and/or cooling the at least one sample;

at least one means for covering the at least one sample comprising at least one movable element for applying force/pressure;

at least one force distribution unit suitable for (i) accommodating a force/pressure as exerted onto the at least one force distribution unit by the at least one movable element that is part of the at least one means for covering, and for (ii) redistributing and/or redirecting said force/pressure onto the at least one sample and/or the at least one means of accommodating the at least one sample, characterized in that the at least one force distribution unit comprises at least one medium or material, which is a fluid, that is unable to withstand a static shear stress and deforms continuously under the action of a shear force:

wherein the at least one medium or material of the at least one force distribution unit is contained within a containment that has at least one deformable contact area that is capable of changing shape in accordance with a change in the shape of said at least one medium or material, wherein said containment is capable to contain said at least one medium or material during said change of shape, and wherein an array of elevated areas is located inside the containment, wherein the at least one medium or material of the containment is in fluidic contact with a pressure reservoir outside the containment.

2. The device according to claim 1, wherein the at least one medium or material of the at least one force distribution unit has a shear modulus of less than 1 GPa.

3. The device according to claim 1, wherein the at least one medium or material of the at least one force distribution unit has a viscosity at 25° C. of less than 1000 Pas.

4. The device according to any one of claims 1-3, wherein the at least one medium or material of the at least one force distribution unit is a liquid, a gas, or a gel.

5. The device according to claim 1, wherein the array of elevated areas forms an array of channels.

6. The device according to claim 1, wherein an intermediate sheet or foil is provided between the at least one sample and the at least one force distribution unit.

7. The device according to claim 1, wherein the at least one means for heating and/or cooling is part of the at least one means for accommodating and/or is part of the at least one means for covering and/or is part of the at least one force distribution unit.

8. The device according to claim 7 wherein the at least one force distribution unit comprises the at least one means for heating and/or cooling, characterized in that said at least one means for heating and/or cooling heats and/or cools the at least one medium or material of the at least one force distribution unit.

9. The device according to claim 1, wherein the at least one means for heating and/or cooling are selected from the group of resistance heater, fluid mediated heating/cooling, air/gas cooling, Peltier heating/cooling, Joule frictional heating and/or radiation heating.

10. The device according to claim 1, wherein the at least one medium or material of the at least one force distribution unit has a thermal conductivity of at least 0.1 $W \cdot m^{-1} \cdot K^{-1}$ at 293 K.

11. A process for controlling a temperature of at least one sample, wherein said process comprises at least the following steps:

(a) placing at least one sample in at least one means for accommodating;

(b) covering the at least one sample with at least one means for covering, wherein the at least one means for covering comprises at least one movable element for applying force/pressure;

(c) accommodating a force/pressure as exerted onto at least one force distribution unit by the at least one movable element and redistributing and/or redirecting a force/pressure as exerted onto the at least one force distribution unit as situated between said at least one means for covering and the at least one sample by at least one medium or material that is unable to withstand a static shear stress and deforms continuously under the action of a shear force and that is part of said at least one force distribution unit, wherein the at least one medium or material of the at least one force distribution unit is contained within a containment that has at least one deformable contact area that is capable of changing shape in accordance with a change in the shape of said at least one medium or material, wherein said containment is capable to contain said medium or material during said change of shape, wherein an array of elevated areas is located inside the containment and wherein the at least one medium or material of the containment is in fluidic contact with a pressure reservoir outside the containment.

12. The process according to claim 11, wherein said at least one means for covering, said at least one force distribution unit and the at least one sample contained in a reaction vessel, are brought in physical contact, thereby establishing direct thermal contact between the at least one force distribution unit and the reaction vessel.

13. The process according to claim 11 or 12, wherein at least two reaction vessels are used that are different from each other in regard to their height.

14. The process according to claim 11 or 12, wherein the at least one means for accommodating accommodates less than the maximum number of reaction vessels that can be accommodated by the at least one means for accommodating.

15. The process according to claim 11, wherein said step of accommodating and redistributing and/or redirecting a force/pressure as exerted onto the at least one force distribution unit comprises (c1) lowering the pressure of the at least one medium or material inside said containment so that the at least one deformable contact area of the containment is brought in physical contact with the array of elevated areas which are located inside said containment;

(c2) bringing the at least one deformable contact area into physical contact with the at least one means for accommodating and increasing the pressure of the at least one medium or material in the containment, so that the at least one deformable contact area is brought in thermal and/or physical contact with the at least one sample and at least a thin film of the at least one medium or material is formed between the array of elevated areas and the at least one deformable contact area.

16. The process according to claim 11, further comprising step (d) performing chemical and/or biological reactions, wherein said step (d) is performed after the step (c).

17. The process according to claim 16, wherein said reaction comprises a temperature sensitive reaction in conjunction with nucleic acid amplification.

18. The process according to claim 17, wherein said reaction comprises the polymerase chain reaction (PCR).

* * * * *